US012702746B2

(12) United States Patent
Brownhill et al.

(10) Patent No.: US 12,702,746 B2
(45) Date of Patent: Aug. 11, 2026

(54) SYSTEMS AND METHODS FOR MEASURING AND TRACKING WOUND VOLUME

(71) Applicant: T.J.Smith and Nephew, Limited, Hull (GB)

(72) Inventors: Varuni Rachindra Brownhill, Swanland (GB); Benjamin James Gardner, Hull (GB); Samuel John Mortimer, Kingston upon Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 295 days.

(21) Appl. No.: 18/656,245

(22) Filed: May 6, 2024

(65) Prior Publication Data

US 2024/0285845 A1 Aug. 29, 2024

Related U.S. Application Data

(63) Continuation of application No. 17/759,502, filed as application No. PCT/EP2021/051264 on Jan. 21, 2021, now Pat. No. 12,011,532.

(30) Foreign Application Priority Data

Jan. 29, 2020 (GB) ..................................... 2001212

(51) Int. Cl.
*A61M 1/00* (2006.01)

(52) U.S. Cl.
CPC ................ *A61M 1/73* (2021.05); *A61M 1/96* (2021.05); *A61M 1/985* (2021.05);
(Continued)

(58) Field of Classification Search
CPC .......... A61M 1/73; A61M 1/985; A61M 1/96; A61M 2205/15; A61M 2205/3331; A61M 2205/3584
(Continued)

(56) References Cited

U.S. PATENT DOCUMENTS

| | | |
|---|---|---|
| 2,923,298 A | 2/1960 | Dockstader et al. |
| 3,972,328 A | 8/1976 | Chen |

(Continued)

FOREIGN PATENT DOCUMENTS

| | | |
|---|---|---|
| DE | 3443101 A1 | 5/1986 |
| DE | 19535537 A1 | 3/1997 |

(Continued)

OTHER PUBLICATIONS

Advantec MFS, Inc., "Membrane Filters" (catalog), retrieved from http://www.advantecmfs.com/catalog/filt/membrane.pdf, on Jan. 29, 2016, Copyright 2001-2011, 17 pages.

(Continued)

*Primary Examiner* — Andrew J Mensh
(74) *Attorney, Agent, or Firm* — Knobbe, Martens, Olson & Bear, LLP

(57) ABSTRACT

A negative pressure wound therapy system can include a negative pressure source configured to provide, via a fluid flow path, negative pressure to a wound covered by a wound dressing. The system can include a controller. The controller can be configured to periodically activate the negative pressure source to maintain negative pressure in the fluid flow path between a low negative pressure setpoint and a high negative pressure setpoint. The controller can be configured to determine a change in a volume of the wound based on a difference between a first time and a second time at which the high negative pressure setpoint has been established in the fluid flow path, the second time being (Continued)

subsequent to the first time. The controller can be configured to provide indication of the change in the volume of the wound.

20 Claims, 9 Drawing Sheets

(52) U.S. Cl.
CPC . *A61M 2205/15* (2013.01); *A61M 2205/3331* (2013.01); *A61M 2205/3584* (2013.01)

(58) Field of Classification Search
USPC ........................................................ 604/543
See application file for complete search history.

(56) References Cited

U.S. PATENT DOCUMENTS 4,029,598 A 6/1977 Neisius et al.
4,728,499 A 3/1988 Fehder
4,813,942 A 3/1989 Alvarez
5,056,510 A 10/1991 Gilman
5,181,905 A 1/1993 Flam
5,238,732 A 8/1993 Krishnan
5,549,584 A 8/1996 Gross
5,707,499 A 1/1998 Joshi et al.
5,759,570 A 6/1998 Arnold
5,852,126 A 12/1998 Barnard et al.
6,071,267 A 6/2000 Zamierowski
6,626,891 B2 9/2003 Ohmstede
6,685,681 B2 2/2004 Lockwood et al.
6,752,794 B2 6/2004 Lockwood et al.
6,936,037 B2 8/2005 Bubb et al.
6,951,553 B2 10/2005 Bubb et al.
6,979,324 B2 12/2005 Bybordi et al.
7,070,584 B2 7/2006 Johnson et al.
7,108,683 B2 9/2006 Zamierowski
7,216,651 B2 5/2007 Argenta et al.
7,361,184 B2 4/2008 Joshi
7,381,859 B2 6/2008 Hunt et al.
7,605,298 B2 10/2009 Bechert et al.
7,615,036 B2 11/2009 Joshi et al.
7,622,629 B2 11/2009 Aali
7,625,362 B2 12/2009 Boehringer et al.
7,700,819 B2 4/2010 Ambrosio et al.
7,718,249 B2 5/2010 Russell et al.
7,722,582 B2 5/2010 Lina et al.
7,749,531 B2 7/2010 Booher
7,759,537 B2 7/2010 Bishop et al.
7,759,539 B2 7/2010 Shaw et al.
7,775,998 B2 8/2010 Riesinger
7,811,269 B2 10/2010 Boynton et al.
7,910,791 B2 3/2011 Coffey
7,922,703 B2 4/2011 Riesinger
7,959,624 B2 6/2011 Riesinger
7,976,519 B2 7/2011 Bubb et al.
8,062,331 B2 11/2011 Zamierowski
8,152,785 B2 4/2012 Vitaris
8,162,907 B2 4/2012 Heagle
8,235,972 B2 8/2012 Adahan
8,241,261 B2 8/2012 Randolph et al.
8,372,049 B2 2/2013 Jaeb et al.
8,372,050 B2 2/2013 Jaeb et al.
8,425,478 B2 4/2013 Olson
8,513,481 B2 8/2013 Gergely et al.
8,540,688 B2 9/2013 Eckstein et al.
8,545,466 B2 10/2013 Andresen et al.
8,568,386 B2 10/2013 Malhi
8,628,505 B2 1/2014 Weston
8,641,691 B2 2/2014 Fink et al.
8,663,198 B2 3/2014 Buan et al.
8,795,243 B2 8/2014 Weston
8,795,800 B2 8/2014 Evans
8,814,841 B2 8/2014 Hartwell
8,905,985 B2 12/2014 Allen et al.
9,012,714 B2 4/2015 Fleischmann
9,067,003 B2 6/2015 Buan et al.
9,127,665 B2 9/2015 Locke et al.
9,220,822 B2 12/2015 Hartwell
9,283,118 B2 3/2016 Locke et al.
9,302,033 B2 4/2016 Riesinger
9,375,521 B2 6/2016 Hudspeth et al.
9,381,283 B2 7/2016 Adams et al.
9,421,309 B2 8/2016 Robinson et al.
9,427,505 B2 8/2016 Askem et al.
9,452,248 B2 9/2016 Blott et al.
9,629,986 B2 4/2017 Patel et al.
9,681,993 B2 6/2017 Wu et al.
9,682,179 B2 6/2017 May
9,795,725 B2 10/2017 Joshi et al.
9,808,561 B2 11/2017 Adie et al.
9,829,471 B2 11/2017 Hammond et al.
9,844,473 B2 12/2017 Blott et al.
9,962,474 B2 5/2018 Greener
10,016,309 B2 7/2018 Hartwell
10,046,096 B2 8/2018 Askem et al.
10,105,471 B2 10/2018 Weston
10,188,555 B2 1/2019 Vitaris et al.
10,201,644 B2 2/2019 Haggstrom et al.
10,328,188 B2 6/2019 Deutsch et al.
10,493,184 B2 12/2019 Collinson et al.
10,881,324 B2 1/2021 Ryu et al.
11,253,401 B2 2/2022 Pratt et al.
11,364,334 B2 6/2022 Long et al.
2002/0087136 A1 7/2002 Widlund
2003/0125646 A1 7/2003 Whitlock
2004/0057855 A1 3/2004 Gerlach et al.
2005/0222544 A1 10/2005 Weston
2006/0009744 A1 1/2006 Erdman et al.
2007/0040454 A1 2/2007 Freudenberger et al.
2007/0225663 A1 9/2007 Watt et al.
2007/0255194 A1 11/2007 Gudnason et al.
2008/0031748 A1 2/2008 Ihle et al.
2008/0132821 A1 6/2008 Propp et al.
2008/0223378 A1 9/2008 Henderson et al.
2009/0125004 A1 5/2009 Shen et al.
2009/0157024 A1 6/2009 Song
2009/0234306 A1 9/2009 Vitaris
2009/0299306 A1 12/2009 Buan
2010/0125258 A1 5/2010 Coulthard et al.
2010/0259406 A1 10/2010 Caso et al.
2010/0318052 A1 12/2010 Ha et al.
2011/0004172 A1 1/2011 Eckstein et al.
2011/0224631 A1 9/2011 Simmons et al.
2012/0051945 A1 3/2012 Orndorff et al.
2013/0066285 A1 3/2013 Locke et al.
2013/0066289 A1 3/2013 Song et al.
2013/0090616 A1 4/2013 Neubauer
2013/0138054 A1 5/2013 Fleischmann
2013/0144227 A1 6/2013 Locke et al.
2013/0150813 A1* 6/2013 Gordon .................. A61M 1/60 604/319
2013/0165878 A1 6/2013 Heagle
2013/0296762 A1 11/2013 Toth
2013/0302545 A1 11/2013 Schnelker et al.
2014/0114268 A1 4/2014 Auguste et al.
2014/0200533 A1 7/2014 Whyte et al.
2014/0316359 A1 10/2014 Collinson et al.
2015/0032035 A1 1/2015 Banwell et al.
2015/0119831 A1 4/2015 Robinson et al.
2015/0119832 A1 4/2015 Locke
2015/0119833 A1 4/2015 Coulthard et al.
2016/0000611 A1 1/2016 Niederauer et al.
2016/0101278 A1* 4/2016 Norris .................. A61M 39/22 604/29
2016/0298620 A1 10/2016 Cordoba et al.
2017/0128642 A1 5/2017 Buan
2017/0368239 A1* 12/2017 Askem .................. A61M 1/743
2018/0104391 A1* 4/2018 Luxon .................. A61M 1/742
2018/0133378 A1 5/2018 Askem et al.
2018/0318476 A1 11/2018 Askem et al.
2019/0192744 A1 6/2019 Greener et al.
2019/0298579 A1* 10/2019 Moore .................. A61M 3/022
2020/0061253 A1* 2/2020 Long .................... A61M 1/964

(56) References Cited

U.S. PATENT DOCUMENTS

| | | | | |
|---|---|---|---|---|
| 2020/0121833 | A9 | 4/2020 | Askem et al. | |
| 2020/0139023 | A1 | 5/2020 | Haggstrom et al. | |
| 2020/0246194 | A1 | 8/2020 | Gonzalez et al. | |
| 2020/0306422 | A1 | 10/2020 | Moore et al. | |
| 2021/0085838 | A1 * | 3/2021 | Locke | A61M 1/96 |

FOREIGN PATENT DOCUMENTS

| | | | | |
|---|---|---|---|---|
| DE | 19700271 | A1 | 9/1997 | |
| DE | 202004017052 | U1 | 6/2005 | |
| EP | 0091800 | A1 | 10/1983 | |
| EP | 0122042 | A2 | 10/1984 | |
| EP | 0340018 | A2 | 11/1989 | |
| EP | 0999858 | B1 | 9/2004 | |
| EP | 1476217 | B1 | 3/2008 | |
| EP | 1955887 | A2 | 8/2008 | |
| EP | 2140968 | A2 | 1/2010 | |
| EP | 2462908 | A1 | 6/2012 | |
| EP | 3257438 | A1 * | 12/2017 | A61B 5/103 |
| EP | 2821035 | B1 | 12/2019 | |
| EP | 3269404 | B1 | 10/2020 | |
| EP | 4096735 | A1 | 12/2022 | |
| FR | 1163907 | A | 10/1958 | |
| GB | 1255395 | A | 12/1971 | |
| GB | 2093190 | A | 8/1982 | |
| GB | 2307180 | B | 6/2000 | |
| GB | 2468905 | A | 9/2010 | |
| WO | WO-8300742 | A1 | 3/1983 | |
| WO | WO-9216245 | A1 | 10/1992 | |
| WO | WO-9605873 | A1 | 2/1996 | |
| WO | WO-0134223 | A1 | 5/2001 | |
| WO | WO-03045492 | A1 | 6/2003 | |
| WO | WO-2004060148 | A2 | 7/2004 | |
| WO | WO-2004077387 | A1 | 9/2004 | |
| WO | WO-2005046760 | A1 | 5/2005 | |
| WO | WO-2005105180 | A1 | 11/2005 | |
| WO | WO-2006052338 | A2 | 5/2006 | |
| WO | WO-2007015964 | A1 | 2/2007 | |
| WO | WO-2007059742 | A1 | 5/2007 | |
| WO | WO-2007085396 | A1 | 8/2007 | |
| WO | WO-2007113597 | A2 | 10/2007 | |
| WO | WO-2007118652 | A1 | 10/2007 | |
| WO | WO-2008039223 | A1 | 4/2008 | |
| WO | WO-2009019227 | A2 | 2/2009 | |
| WO | WO-2009060097 | A2 | 5/2009 | |
| WO | WO-2009124100 | A1 | 10/2009 | |
| WO | WO-2009145703 | A1 | 12/2009 | |
| WO | WO-2009147402 | A2 | 12/2009 | |
| WO | WO-2009158128 | A2 | 12/2009 | |
| WO | WO-2010142959 | A2 | 12/2010 | |
| WO | WO-2011135285 | A1 | 11/2011 | |
| WO | WO-2011135286 | A1 | 11/2011 | |
| WO | WO-2011135287 | A1 | 11/2011 | |
| WO | WO-2011144888 | A1 | 11/2011 | |
| WO | WO-2012131237 | A1 | 10/2012 | |
| WO | WO-2012143665 | A1 | 10/2012 | |
| WO | WO-2013010907 | A1 | 1/2013 | |
| WO | WO-2013064852 | A1 | 5/2013 | |
| WO | WO-2013083800 | A1 | 6/2013 | |
| WO | WO-2013090810 | A1 | 6/2013 | |
| WO | WO-2013149078 | A1 | 10/2013 | |
| WO | WO-2014008348 | A2 | 1/2014 | |
| WO | WO-2014016759 | A1 | 1/2014 | |
| WO | WO-2014020440 | A1 | 2/2014 | |
| WO | WO-2014020443 | A2 | 2/2014 | |
| WO | WO-2014108476 | A1 | 7/2014 | |
| WO | WO-2015022334 | A1 | 2/2015 | |
| WO | WO-2015022340 | A1 | 2/2015 | |
| WO | WO-2016018448 | A1 | 2/2016 | |
| WO | WO-2016174048 | A1 | 11/2016 | |
| WO | WO-2018096390 | A1 | 5/2018 | |
| WO | WO-2018164803 | A1 | 9/2018 | |
| WO | WO-2019023311 | A1 | 1/2019 | |

OTHER PUBLICATIONS

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

International Preliminary Report on Patentability for Application No. PCT/EP2021/051264, mailed on Aug. 11, 2022, 9 pages.

International Search Report and Written Opinion for Application No. PCT/EP2021/051264, mailed on Mar. 29, 2021, 15 pages.

Kendall Ultec Hydrocolloid Dressing (4"x4"), Product Ordering Page, web page downloaded on Jul. 13, 2014, 1 page.

Protz K., "Modern Wound Dressings Support the Healing Process," Wound care: Indications and Application, Geriatrie Journal, Apr. 2005, pp. 3333-3339 (17 pages with English translation).

Smith & Nephew, "PICO Single Use Negative Pressure Wound Therapy System," Spiral Booklet, Mar. 2011, 7 pages.

Technology Watch, May 1989, 1 page.

Affidavit of Dr. Viktoria Skeppstedt filed in the Opposition against European Patent No. 4223265, dated May 19, 2025, 2 pages.

Allevyn Adhesive., "SMTL Dressings Datacard," Smith and Nephew Healthcare Ltd, last modified May 11, 2007, 3 pages.

Anonymous, "3M Tegaderm Transparent Film Dressings—Product Profile," Retrieved from http://multimedia.3m.com/mws/media/4479830/tegaderm-transparent-film-dressing-brochure.pdf, Jan. 1, 2012, 8 pages.

Bartels V.T., "Handbook of Medical Textiles," © Woodhead Publishing Limited, 2011, 115 pages.

Declaration of Chris Locke Submitted in the Opposition against European Patent No. 2231221, mailed on Sep. 7, 2016, 1 page.

Definition of "Strand," Collins English Dictionary, accessed Apr. 11, 2024, 15 pages, URL: https://www.collinsdictionary.com/dictionary/english/strand.

Definition of "System," Cambridge Dictionary, accessed Apr. 11, 2024, 8 pages, URL:https://dictionary.cambridge.org/dictionary/english/system.

Du Pont, "Material Safety Data Sheet—Dupont Spunlaced Nonwoven Fabric Version 2.0", revision date May 5, 2009, filed in the Opposition against European Patent No. 3628289 on Aug. 8, 2025, 5 pages.

"Search Results from UK Intellectual Property Office Trade Mark Register," filed in the Opposition for the European Patent No. 4023197 on Dec. 15, 2023, 3 pages.

EN 13726-2:2002. "Test methods for primary wound dressings—Part 2: Moisture vapour transmission rate of permeable film dressings," Brussels: European Committee for Standardization (CEN), 2002., 11 pages.

"Handbook of Medical Textiles," Woodhead Publishing Limited, 2011, 41 pages.

Hutten I.M., "Introduction to Nonwoven Filter Media", in Handbook of Nonwoven Filter Media, 2007, 1 page.

Merriam-Webster, Definition of "Port", Retrieved from the Internet: https://www.merriam-webster.com/dictionary/port?src=search-dietbox, Accessed on Feb. 7, 2025, 1 page.

Merriam-Webster, Definition of Port, retrieved from URL: https://www.merriam-webster.com/dictionary/port, on Oct. 26, 2020, 6 pages.

Phan T T., et al., "Evaluation of cell culture on the polyurethane-based membrane (Tegaderm): implication for tissue engineering of skin," Cell Tissue Bank. 2005; 6(2), 1 page.

Riedel E., et al., "Verbandstoff-Fibel," 5. Auflage, Stuttgart, 1995, Seiten 23-35 and 82-95.

Russell S.J., et al., "18—Anisotropic Fluid Transmission in Nonwoven Wound Dressings," Proceedings of the 2nd International Conference, Aug. 24 & 25, 1999, Woodhead Publishing Series in Textiles, 2001, 1 page.

Saul D Harrison & Sons PLC, "DuPont Sontara—Wiping solutions" [brochure], filed in the Opposition against European Patent No. 3628289 on Aug. 8, 2025, 4 pages.

Silverlon, "Negative Pressure Contact Dressings," retrieved from Internet URL: https://www.silverlon.com/products/negative-pressure-contact-dressings , accessed on Jan. 24, 2022, 10 pages.

(56) References Cited

OTHER PUBLICATIONS

"Technical datasheet for the Chem-PositeTM 11C-450 material," Emerging Technologies, filed in the Opposition for the European Patent No. 4023197 on Apr. 29, 2024 (publication date unknown), 1 page.
"The Allevyn Wound Dressings Range" 1 page, Product brochure obtained from: https://www.smith-nephew.com/en-pb/health-care-professionals/products/advanced-wound-management/allevynborder-gilobal-new#relatedtechnologies.
The Wayback Machine, "Cellulose fiber," Extract from Wikipedia, the free encyclopedia, Retrieved from the Internet: URL: http://en.wikipedia.org/wiki/Cellulose_fiber, Online, on 2009, 1 page.
The Wayback Machine, "Rayon Fiber," Extract from Conservation and Art Material Encyclopaedia Online, on Mar. 13, 2006, 1 page.
"Strand," Wiktionary, last edited Mar. 25, 2024 (accessed Apr. 11, 2024), 10 pages, URL: https://en.wiktionary.org/wiki/strand.
Wikipedia, Definition of "Rayon" being Regenerated Cellulose, Retrieved from the Internet: https://en.wikipedia.org/wiki/Rayon, on Feb. 7, 2025, 1 page.

* cited by examiner

SYSTEMS AND METHODS FOR MEASURING AND TRACKING WOUND VOLUME

This application is a continuation of U.S. application Ser. No. 17/759,502, filed Jul. 26, 2022, which is a U.S. national stage application of International Patent Application No. PCT/EP2021/051264, filed Jan. 21, 2021, which claims priority to U.K. Provisional Application No. 2001212.6 filed on Jan. 29, 2020; the disclosure of each of which is hereby incorporated by reference in its entirety.

TECHNICAL FIELD

Embodiments described herein relate to apparatuses, systems, and methods for the treatment of wounds, for example using dressings in combination with negative pressure wound therapy.

DESCRIPTION OF THE RELATED ART

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing.

SUMMARY

A negative pressure wound therapy apparatus can include a negative pressure source. The negative pressure source can be configured to be fluidically connected by a fluid flow path to a wound covered by a wound dressing. The negative pressure source can be configured to provide negative pressure to the wound via the fluid flow path. The apparatus can include a controller. The controller can be configured to periodically activate the negative pressure source to maintain negative pressure in the fluid flow path between a low negative pressure setpoint (or set point) and a high negative pressure setpoint (or set point). The high negative pressure setpoint can be associated with higher level of negative pressure than the low negative pressure setpoint. The controller can be configured to determine a change in a volume of the wound based on a difference between a first time and a second time at which the high negative pressure setpoint has been established in the fluid flow path, the second time being subsequent to the first time. The controller can be configured to provide indication of the change in the volume of the wound.

The negative pressure wound therapy apparatus of any of the preceding paragraphs and/or any of the apparatuses, systems, or devices disclosed herein can include one or more of the following features. The controller can be configured to determine the change in the volume of the wound based on a difference between the first time and the second time divided by the second time. The apparatus can include a pressure sensor configured to measure pressure in the fluid flow path. The controller can be configured to deactivate the negative pressure source in response to a determination that negative pressure in the fluid flow path measured by the pressure sensor satisfies the high negative pressure setpoint. The controller can be configured to activate the negative pressure source in response to a determination that negative pressure in the fluid flow path measured by the pressure sensor satisfies the low negative pressure setpoint. The controller can be configured to monitor the change in the volume of the wound over a duration of time and provide indication of progress of healing of the wound based on the monitored change in the volume of the wound.

A negative pressure wound therapy apparatus can include a negative pressure source. The negative pressure source can be configured to be fluidically connected by a fluid flow path to a wound covered by a wound dressing. The negative pressure source can be configured to provide negative pressure to the wound via the fluid flow path. The apparatus can include a pressure sensor configured to measure pressure in the fluid flow path. The apparatus can include a controller. The controller can be configured to determine a volume of the wound based on a first plurality of negative pressure readings in the fluid flow path measured by the pressure sensor at a first plurality of times and a rate of flow of fluid in the fluid flow path. The controller can be configured to provide indication of the volume of the wound.

The negative pressure wound therapy apparatus of any of the preceding paragraphs and/or any of the apparatuses, systems, or devices disclosed herein can include one or more of the following features. The controller can be configured to monitor change in the volume of the wound over a duration of time and provide indication of progress of healing of the wound based on the monitored change in the volume of the wound. The rate of flow of fluid in the fluid flow path can be set by or correspond to a flow rate of the negative pressure source. The first plurality of negative pressure readings can include first and second negative pressure readings taken by the pressure sensor, respectively, at first and second times. The second time can be subsequent to the first time. The second negative pressure reading can correspond to pressure that is more negative than the first negative pressure reading. The controller can be configured to determine the volume of the wound based on a product of the rate of flow of fluid in the fluid flow path and a difference between the second and first times divided by a difference between the second and first negative pressure readings. The product of the rate of flow of fluid in the fluid flow path and the difference between the second and first times can be scaled by at least one of an ambient temperature or gas constant.

The negative pressure wound therapy apparatus of any of the preceding paragraphs and/or any of the apparatuses, systems, or devices disclosed herein can include one or more of the following features. The controller can be configured to determine a leak rate in the fluid flow path. The controller can be configured to determine the volume of the wound based on the first plurality of negative pressure readings in the fluid flow path measured at the first plurality of times and an adjusted rate of flow of fluid in the fluid flow path. The adjusted rate of flow of fluid in the fluid flow path can be determined based on subtracting the leak rate from the rate of flow of fluid in the fluid flow path. The controller can be configured to determine the leak rate in the fluid flow path based on the volume of the wound and a second plurality of negative pressure readings in the fluid flow path measured at a second plurality of times. The second plurality of negative pressure readings can include third and fourth negative pressure readings taken, respectively, at third and fourth times. The fourth time can be subsequent to the third time. The fourth negative pressure reading can correspond to pressure that is more positive than the third negative pressure reading. The controller can be configured to determine the leak rate based on a product of the volume of the wound and a difference between the fourth and third negative pressure readings divided by a difference between the fourth and third times. The difference between the fourth and third times can be scaled by at least one of an ambient temperature or gas constant.

The negative pressure wound therapy apparatus of any of the preceding paragraphs and/or any of the apparatuses, systems, or devices disclosed herein can include one or more of the following features. The apparatus can include a flow meter configured to determine the rate of flow of fluid in the fluid flow path. The fluid flow path can include an opening configured to admit fluid into the fluid flow path at a controlled leak rate. The first plurality of negative pressure readings can include first and second negative pressure readings taken, respectively, at first and second times. The second time can be subsequent to the first time. The second negative pressure reading can correspond to pressure that is more positive than the first negative pressure reading. The controller can be configured to determine the volume of the wound based on a product of the controlled leak rate and a difference between the second and first times divided by a difference between the second and first negative pressure readings. The product of the controlled leak rate and the difference between the second and first times can be scaled by at least one of an ambient temperature or gas constant.

The negative pressure wound therapy apparatus of any of the preceding paragraphs and/or any of the apparatuses, systems, or devices disclosed herein can include one or more of the following features. The controller can be configured to determine the rate of flow of fluid in the fluid flow path based on the volume of the wound and a second plurality of negative pressure readings in the fluid flow path measured at a second plurality of times. The second plurality of negative pressure readings can include third and fourth negative pressure readings taken, respectively, at third and fourth times. The fourth time can be subsequent to the third time. The fourth negative pressure reading can correspond to pressure that is more negative than the third negative pressure reading. The controller can be configured to determine the rate of flow of fluid in the fluid flow path based on a product of the volume of the wound and a difference between the fourth and third negative pressure readings divided by a difference between the fourth and third times. The difference between the fourth and third times can be scaled by at least one of an ambient temperature or gas constant.

The negative pressure wound therapy apparatus of any of the preceding paragraphs and/or any of the apparatuses, systems, or devices disclosed herein can include one or more of the following features. The controller is can be configured to periodically activate the negative pressure source to maintain negative pressure in the fluid flow path between a low negative pressure setpoint and a high negative pressure setpoint. The high negative pressure setpoint can be associated with higher level of negative pressure than the low negative pressure setpoint. The controller can be configured to activate the negative pressure source in response to a determination that negative pressure in the fluid flow path measured by the pressure sensor satisfies the low negative pressure setpoint. The controller can be configured to deactivate the negative pressure source in response to a determination that negative pressure in the fluid flow path measured by the pressure sensor satisfies the high negative pressure setpoint.

The negative pressure wound therapy apparatus of any of the preceding paragraphs and/or any of the apparatuses, systems, or devices disclosed herein can include one or more of the following features. The controller can adjust the volume of the wound by subtracting volume of one or more of the negative pressure source, canister, one or more lumens or tubes positioned in the fluid flow path, or dressing.

Disclosed are methods of operating a negative pressure wound therapy device of any of the preceding paragraphs and/or any of the apparatuses, systems, or devices disclosed herein.

Any of the features, components, or details of any of the arrangements or embodiments disclosed in this application, including without limitation any of the apparatus embodiments and any of the negative pressure wound therapy embodiments disclosed herein, are interchangeably combinable with any other features, components, or details of any of the arrangements or embodiments disclosed herein to form new arrangements and embodiments.

DETAILED DESCRIPTION

Figure 1:
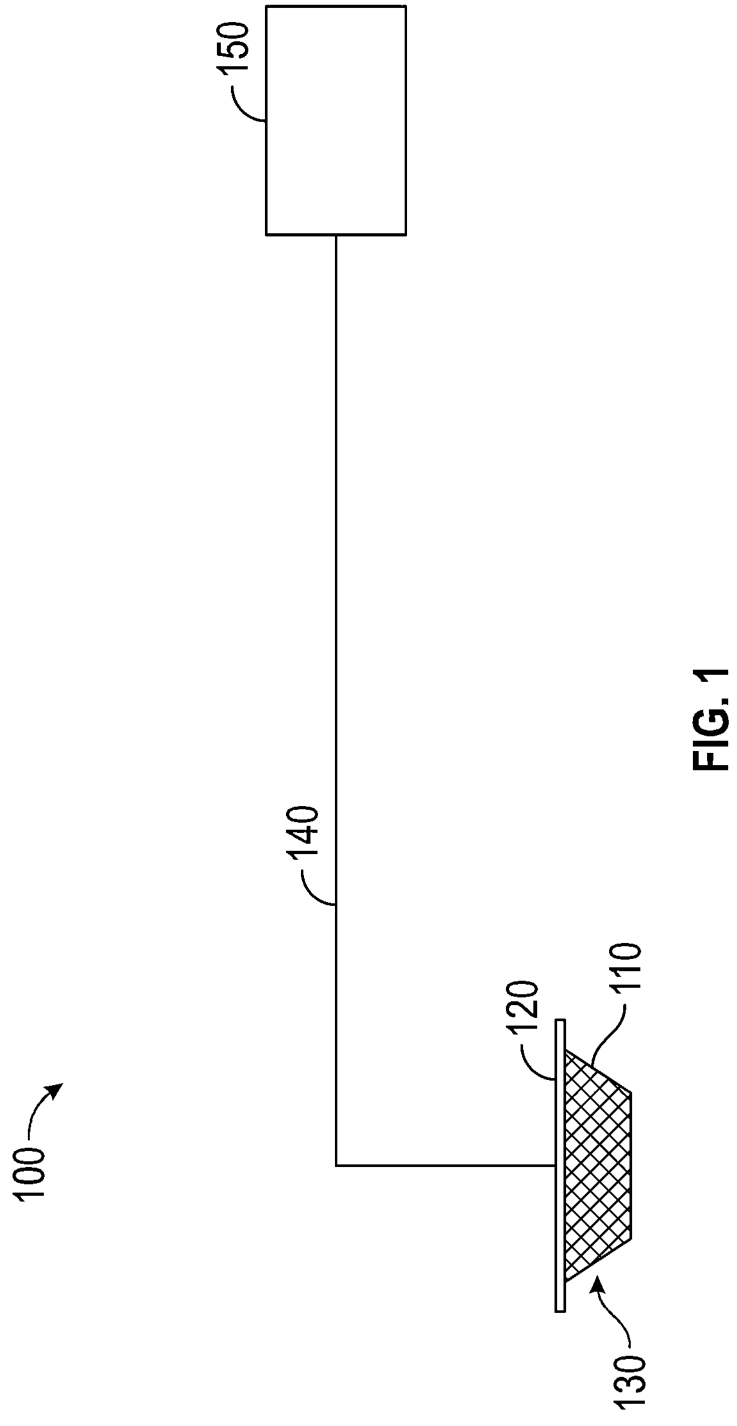
FIG. 1 illustrates a negative pressure wound therapy system.

Embodiments disclosed herein relate to systems and methods of monitoring or treating a wound. Throughout this specification reference is made to a wound. The term wound is to be broadly construed and encompasses open and closed wounds in which skin is torn, cut or punctured or where trauma causes a contusion, or any other superficial or other conditions or imperfections on the skin of a patient or otherwise that benefit from pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

As used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects pressure that is X mmHg below 760 mmHg or, in other words, a pressure of (760−X) mmHg. In addition, negative pressure that is “less” or “smaller” than X mmHg corresponds to pressure that is closer to atmospheric pressure (for example, −40 mmHg is less than −60 mmHg). Negative pressure that is “more” or “greater” than −X mmHg corresponds to pressure that is further from atmospheric pressure (for example, −80 mmHg is more than −60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

A healthcare provider, such as a clinician, nurse, or the like, can provide a TNP prescription specifying, for example, the pressure level or time of application. However, the healing process is different for each patient and the prescription may affect the healing process in a way the clinician or healthcare provider did not expect at the time of devising the prescription. A healthcare provider may try to adjust the prescription as the wound heals (or does not heal), but such process may require various appointments that can be time consuming and repetitive. Embodiments disclosed herein provide systems, devices, or methods of efficiently adjusting TNP prescriptions and delivering effective TNP therapy.

Wound Therapy System

FIG. 1 illustrates a negative pressure wound treatment system 100 (sometimes referred to as a reduced pressure wound therapy system, a TNP system, or a wound treatment system) comprising a wound filler 130 placed inside a wound cavity 110, the wound cavity 110 sealed by a wound cover 120. The wound filler 130 in combination with the wound cover 120 can be referred to as a wound dressing. A conduit 140 (such as a single or multi lumen tube) is connected the wound cover 120 with a wound therapy device 150 (sometimes as a whole or partially referred to as a “pump assembly”) configured to supply reduced or negative pressure. The wound cover 120 can be in fluidic communication with the wound cavity 110.

With any of the systems disclosed herein, a wound therapy device can be canisterless (meaning that exudate is collected in the wound dressing or is transferred via the conduit 140 for collection to another location). However, any of the wound therapy devices disclosed herein can include or support a canister.

Additionally, with any of the wound therapy systems disclosed herein, any of the wound therapy devices can be mounted to or supported by the wound dressing, or adjacent to the wound dressing. The wound filler 130 can be any suitable type, such as hydrophilic or hydrophobic foam, gauze, inflatable bag, and so on. The wound filler 130 can be conformable to the wound cavity 110 such that it substantially fills the wound cavity 110. The wound cover 120 can provide a substantially fluid impermeable seal over the wound cavity 110. In some cases, the wound cover 120 has a top side and a bottom side, and the bottom side adhesively (or in any other suitable manner) seals with the wound cavity 110. The conduit 140 or any other conduit disclosed herein can be formed from polyurethane, PVC, nylon, polyethylene, silicone, or any other suitable material.

The wound cover 120 can have a port (not shown) configured to receive an end of the conduit 140. In some cases, the conduit 140 can otherwise pass through or under the wound cover 120 to supply reduced pressure to the wound cavity 110 so as to maintain a desired level of reduced pressure in the wound cavity 110. The conduit 140 can be any suitable article configured to provide at least a substantially sealed fluid flow pathway or path between the wound therapy device 150 and the wound cover 120, so as to supply the reduced pressure provided by the wound therapy device 150 to wound cavity 110.

The wound cover 120 and the wound filler 130 can be provided as a single article or an integrated single unit. In some cases, no wound filler is provided and the wound cover by itself may be considered the wound dressing. The wound dressing may then be connected, via the conduit 140, to a source of negative pressure of the wound therapy device 150. In some cases, though not required, the wound therapy device 150 can be miniaturized and portable, although larger conventional pumps such can also be used.

The wound cover 120 can be located over a wound site to be treated. The wound cover 120 can form a substantially sealed cavity or enclosure over the wound site. The wound cover 120 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate.

The wound therapy system can operate with or without the use of an exudate canister. The wound therapy system can support an exudate canister. In some cases, configuring the wound therapy device 150 and conduit 140 so that the conduit 140 can be quickly and easily removed from the wound therapy device 150 can facilitate or improve the process of wound dressing or pump changes, if necessary. Any of the pump assemblies disclosed herein can have any suitable connection between the conduit 140 and the pump.

The wound therapy device 150 can deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even-150 mmHg, can be supplied by the wound therapy device 150.

The wound therapy device 150 can provide continuous or intermittent negative pressure therapy. Continuous therapy can be delivered at above 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points (sometimes referred to as set-point). Low set point can be set at above 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above-25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values.

In operation, the wound filler 130 can be inserted into the wound cavity 110, and wound cover 120 can be placed so as to seal the wound cavity 110. The wound therapy device 150 can provide negative pressure to the wound cover 120, which may be transmitted to the wound cavity 110 via the wound filler 130. Fluid (such as, wound exudate) can be drawn through the conduit 140 and stored in a canister. In some cases, fluid is absorbed by the wound filler 130 or one or more absorbent layers (not shown).

Wound dressings that may be utilized with the pump assembly and systems of the present application include Renasys-F, Renasys-G, Renasys AB, and Pico Dressings available from Smith & Nephew. Further description of such wound dressings and other components of a negative pressure wound therapy system that may be used with the pump assembly and systems of the present application are found in U.S. Patent Publication Nos. 2012/0116334, 2011/0213287, 2011/0282309, 2012/0136325 and U.S. Pat. No. 9,084,845, each of which is incorporated by reference in its entirety. In some cases, other suitable wound dressings can be utilized.

Figure 2A:
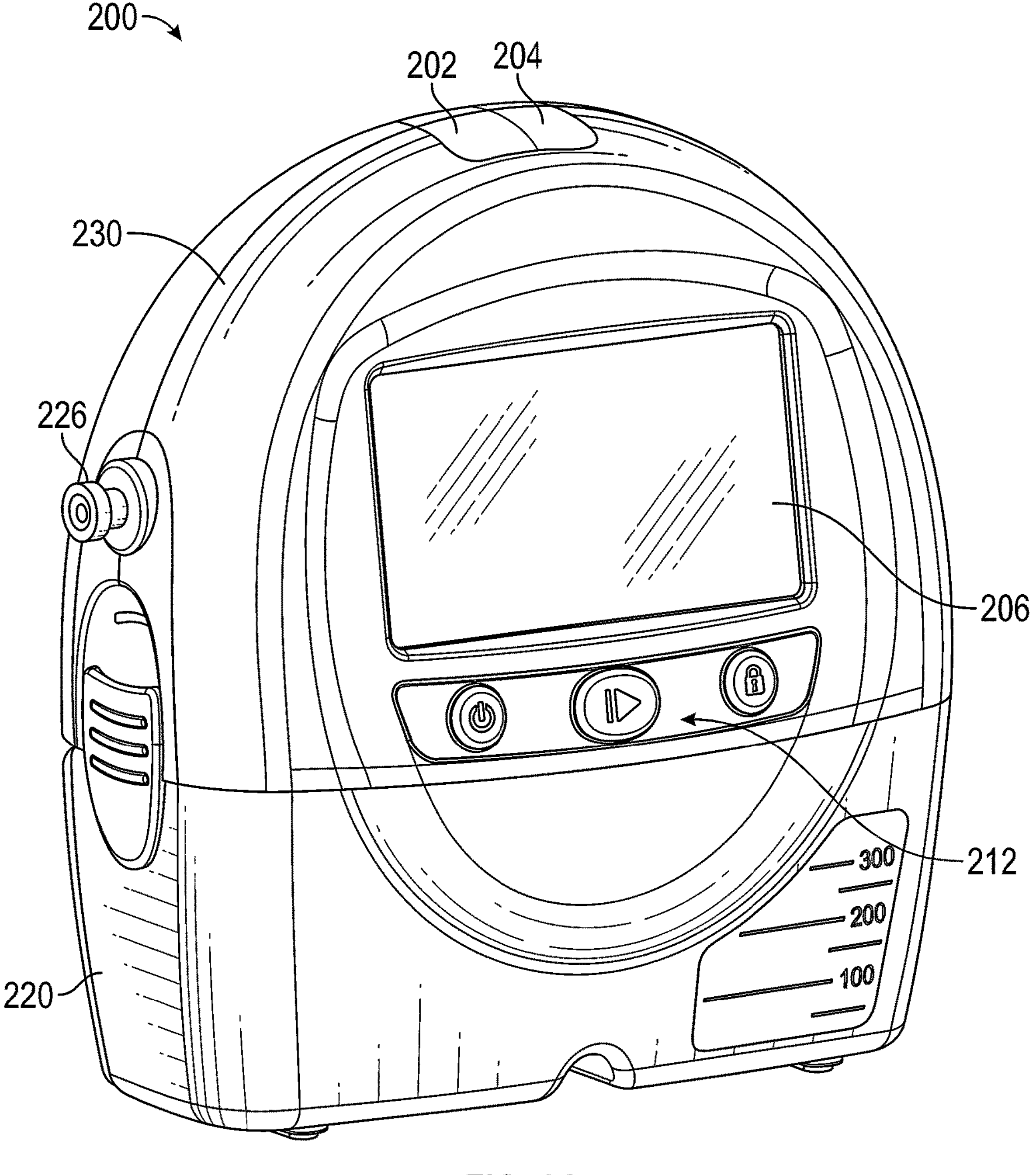
FIGS. 2A and 2B illustrate a negative pressure wound therapy device and canister.
Figure 2B:
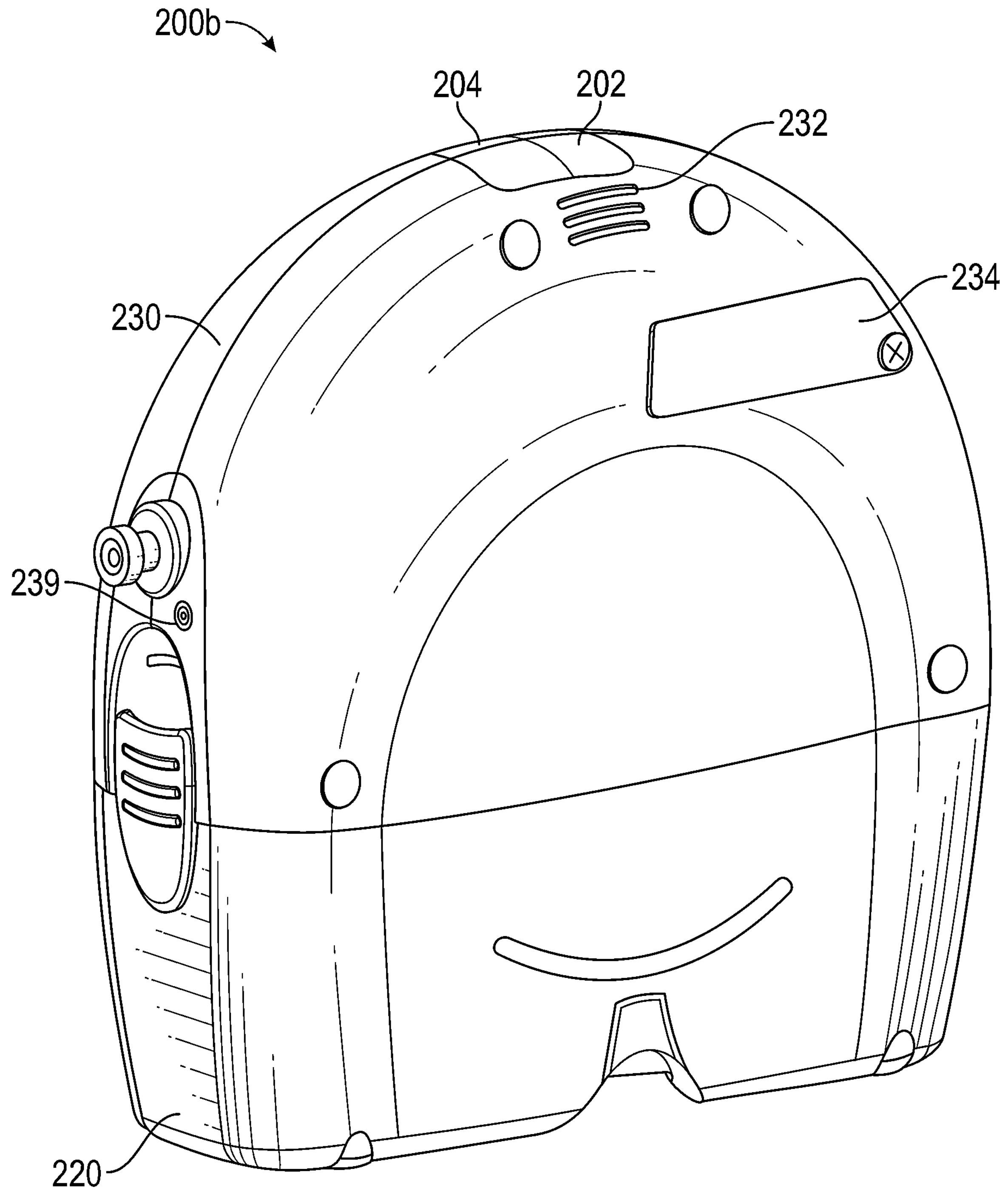

FIGS. 2A and 2B illustrates a negative pressure wound therapy device 200 (sometimes referred to as a wound therapy device) including a pump assembly 230 and a canister 220. As illustrated, the pump assembly 230 and the canister 220 can be connected, thereby forming the wound therapy device 200. The pump assembly 230 can include one or more indicators, such as visual indicator 202 configured to indicate alarms and visual indicator 204 configured to indicate status of the pump assembly 230. The visual indicators 202 and 204 can alert a user (for example, patient, health care provider, or the like) to a variety of operating or failure conditions of the pump assembly 230, including alerting the user to normal or proper operating conditions, pump failure, power supplied to the pump or power failure, detection of a leak within the wound cover or flow pathway (sometimes referred to as fluid flow path), suction blockage in the flow pathway, canister full, overpressure, or any other similar or suitable conditions or combinations thereof. Any one or more suitable indicators can be additionally or alternatively used, such as visual, audio, tactile indicator, and so on.

The pump assembly 230 can include a display 206 (such as a screen) mounted in a recess formed in a case of the pump assembly 230. The display 206 can be a touch screen display. The display 206 can support playback of audiovisual (AV) content, such as instructional videos, and render a number of screens or graphical user interfaces (GUIs) for configuring, controlling, and monitoring the operation of the pump assembly 230. The pump assembly 230 can include one or more strap mounts 226 for connecting a carry strap to the pump assembly 230 or for attaching a cradle. The canister 220 may be replaced with another canister, such as when the canister 220 has been filled with fluid.

The pump assembly 230 can include buttons 212 (such as keys) that allow the user to operate and monitor the operation of the pump assembly 230. One of the buttons 212 can operate as a power button to turn on/off the pump assembly 230. Another of the buttons 212 can operate as a play/pause button for the delivery of therapy.

The canister 220 can hold fluid (such as, exudate) removed from the wound cavity 110. The canister 220 includes one or more latches for attaching the canister to the pump assembly 230. For example, the canister 220 as illustrated can have a capacity of 300 mL and include graduations. The canister 220 can include a tubing channel for connecting to the conduit 140.

FIG. 2B illustrates a rear view 200B of the pump assembly 230 and the canister 220. The pump assembly 230 can include a speaker 232 for producing sound. The speaker 232 can generate an acoustic alarm in response to deviations in therapy delivery, non-compliance with therapy delivery, or any other similar or suitable conditions or combinations thereof.

The pump assembly 230 can include a filter access door 234 for accessing and replacing one or more filters, such as antibacterial filters. The pump assembly 230 can comprise a power jack 239 for charging and recharging an internal battery of the pump assembly. The pump assembly 230 can include a disposable power source, such as batteries, so that no power jack is needed.

Figure 3:
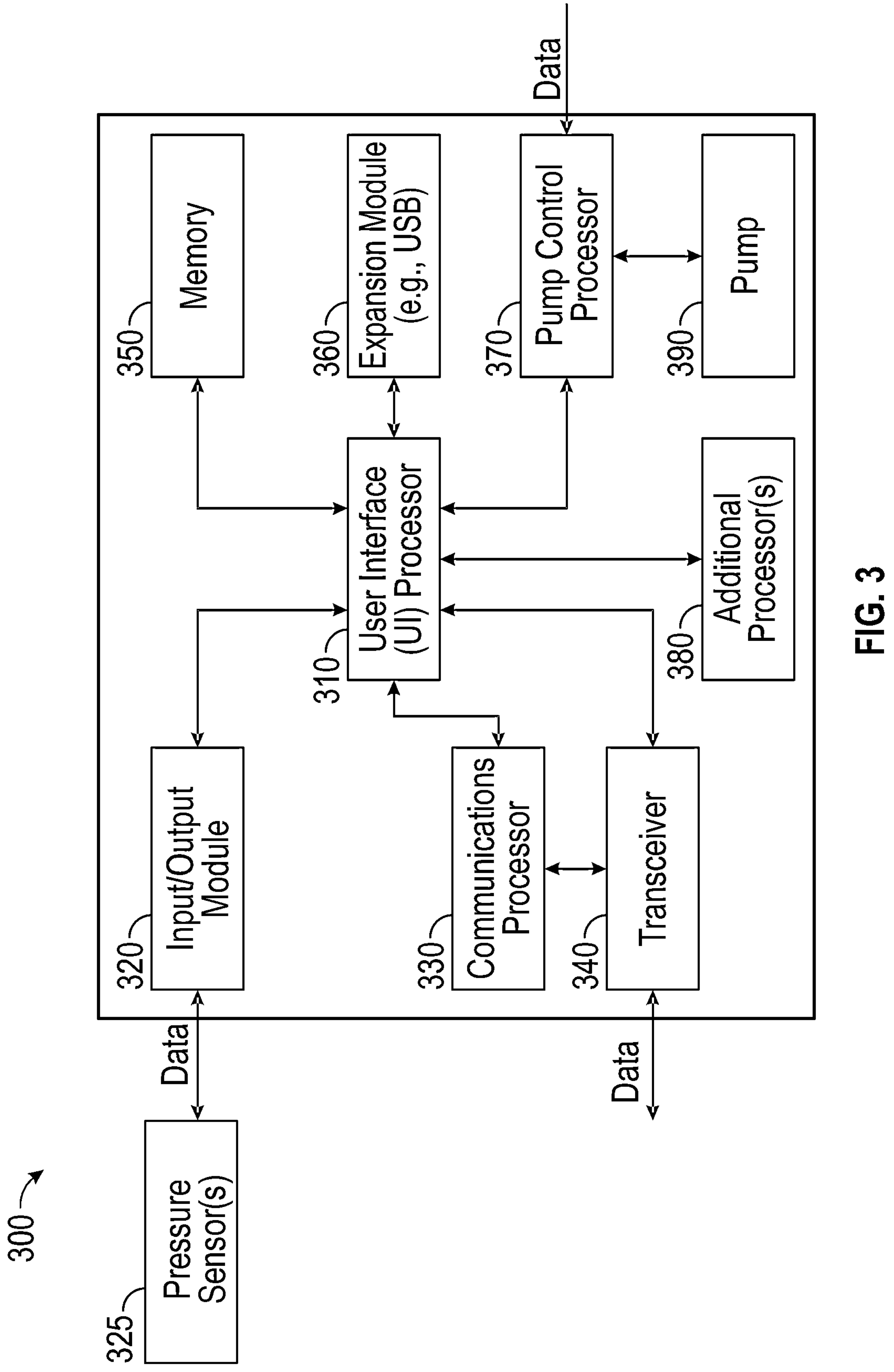
FIG. 3 illustrates a schematic of a negative pressure wound therapy device.

FIG. 3 illustrates a schematic of a control system 300 which can be employed in the wound monitoring or treatment systems described herein, such as in the wound therapy device 200 of FIGS. 2A and 2B. Electrical components can operate to accept user input, provide output to the user, operate the pressure source, provide network connectivity, and so on. A first processor can be responsible for user activity, and a second processor can be responsible for controlling another device, such as a pump 390.

Input and output to the other device, such as a pump 390, one or more sensors (for example, one or more pressure sensors 325 configured to monitor pressure in one or more locations of the fluid flow path), or the like, can be controlled by an input/output (I/O) module 320. For example, the I/O module can receive data from one or more sensors through one or more ports, such as serial (for example, I2C), parallel, hybrid ports, and the like.

The processor 310 can receive data from and provide data to one or more expansion modules 360, such as one or more USB ports, SD ports, Compact Disc (CD) drives, DVD drives, Fire Wire ports, Thunderbolt ports, PCI Express ports, and the like. The processor 310, along with other controllers or processors, can store data in memory 350 (such as one or more memory modules), which can be internal or external to the processor 310. Any suitable type of memory can be used, including volatile or non-volatile memory, such as RAM, ROM, magnetic memory, solid-state memory, Magnetoresistive random-access memory (MRAM), and the like.

The processor 310 can be a general purpose controller, such as a low-power processor, or an application specific processor. The processor 310 can be configured as a "central" processor in the electronic architecture of the control system 300, and the processor 310 can coordinate the activity of other processors, such as a pump control processor 370, communications processor 330, and one or more additional processors 380. The processor 310 can run a suitable operating system, such as a Linux, Windows CE, VxWorks, etc.

The pump control processor 370 can control the operation of a pump 390, which can generate negative or reduced pressure. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump control processor 370 can measure pressure in a fluid flow path, using data received from one or more pressure sensors 325, calculate the rate of fluid flow, and control the pump. The pump control processor 370 can control the pump motor so that a desired level of negative pressure in achieved in the wound cavity 110. The desired level of negative pressure can be pressure set or selected by the user. The pump control processor 370 can control the pump (for example, pump motor) using pulse-width modulation (PWM). A control signal for driving the pump can be a 0-100% duty cycle PWM signal. The pump control processor 370 can perform flow rate calculations and detect alarms. The pump control processor 370 can communicate information to the processor 310. The pump control processor 370 can be a low-power processor.

A communications processor 330 can provide wired or wireless connectivity. The communications processor 330 can utilize one or more transceivers 340 for sending and receiving data. The one or more transceivers 340 can include one or more antennas, optical sensors, optical transmitters, vibration motors or transducers, vibration sensors, acoustic sensors, ultrasound sensors, or the like. The communications processor 330 can provide one or more of the following types of connections: Global Positioning System (GPS), cellular connectivity (for example, 2G, 3G, LTE, 4G, 5G, or the like), near field communication (NFC), Bluetooth connectivity, radio frequency identification (RFID), wireless local area network (WLAN), wireless personal area network (WPAN), WiFi connectivity, Internet connectivity, optical connectivity (for example, using infrared light, barcodes, such as QR codes, etc.), acoustic connectivity, ultrasound connectivity, or the like. Connectivity can be used for various activities, such as pump assembly location tracking, asset tracking, compliance monitoring, remote selection, uploading of logs, alarms, and other operational data, and adjustment of therapy settings, upgrading of software or firmware, pairing, and the like.

The communications processor 330 can provide dual GPS/cellular functionality. Cellular functionality can, for example, be 3G, 4G, or 5G functionality. The communications processor 330 can communicate information to the processor 310. The communications processor 330 can include internal memory or can utilize memory 350. The communications processor 330 can be a low-power processor.

The control system 300 can store data, such as GPS data, therapy data, device data, and event data. This data can be stored, for example, in memory 350. This data can include patient data collected by one or more sensors. The control system 300 can track and log therapy and other operational data. Such data can be stored, for example, in the memory 350.

Using the connectivity provided by the communications processor 330, the control system 300 can upload any of the data stored, maintained, or tracked by the control system 300 to a remote computing device. The control system 300 can also download various operational data, such as therapy selection and parameters, firmware and software patches and upgrades, and the like. The one or more additional processors 380, such as processor for controlling one or more user interfaces (such as, one or more displays), can be utilized. In some cases, any of the illustrated or described components of the control system 300 can be omitted depending on an embodiment of a wound monitoring or treatment system in which the control system 300 is used.

Any of the negative pressure wound therapy devices described herein can include one or more features disclosed in U.S. Pat. No. 9,737,649 or U.S. Patent Publication No. 2017/0216501, each of which is incorporated by reference in its entirety.

Canisterless Pump Assembly

Figures 4A, 4B:
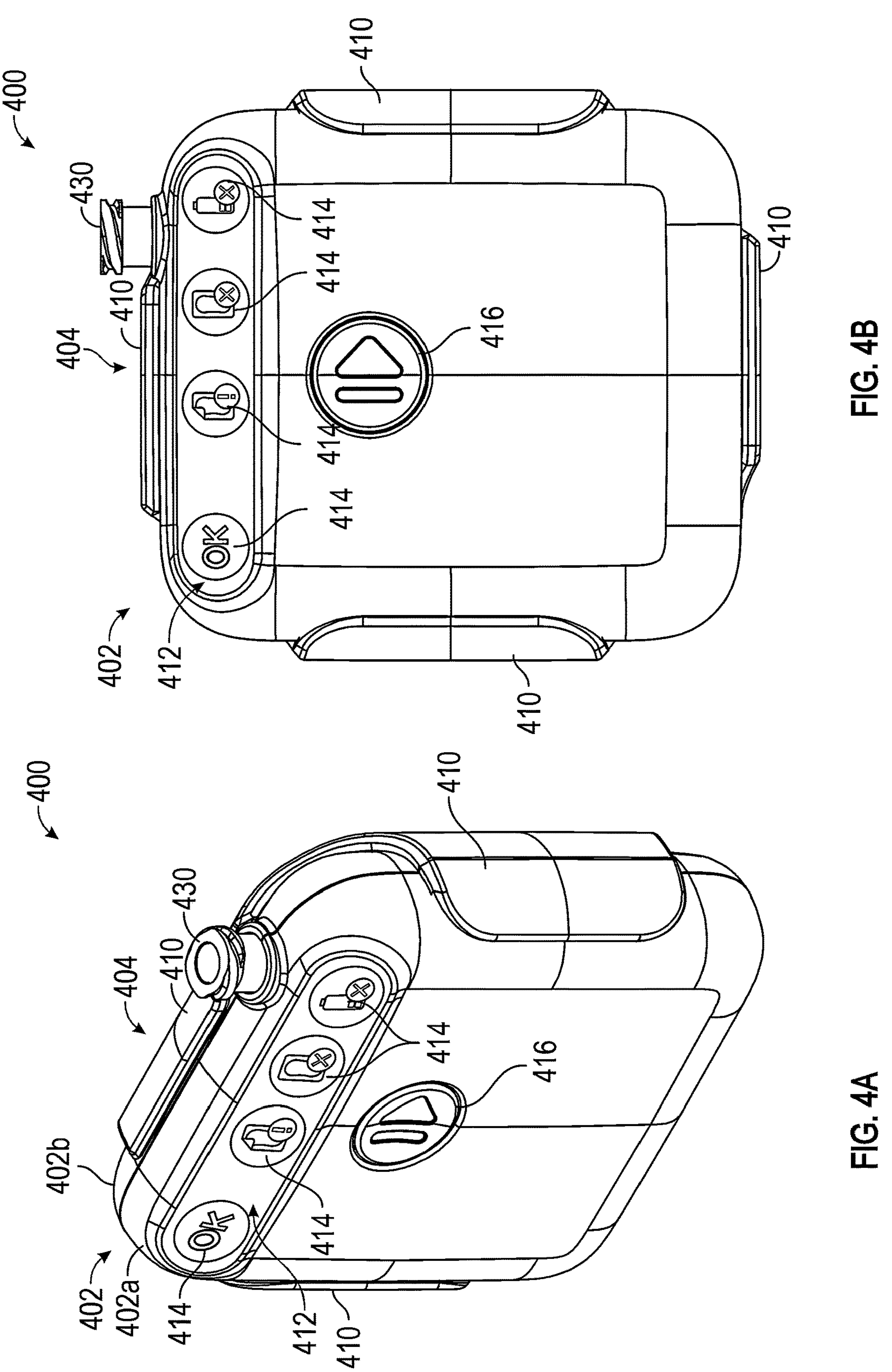
FIGS. 4A, 4B, and 4C illustrate a negative pressure wound therapy device.
Figure 4C:
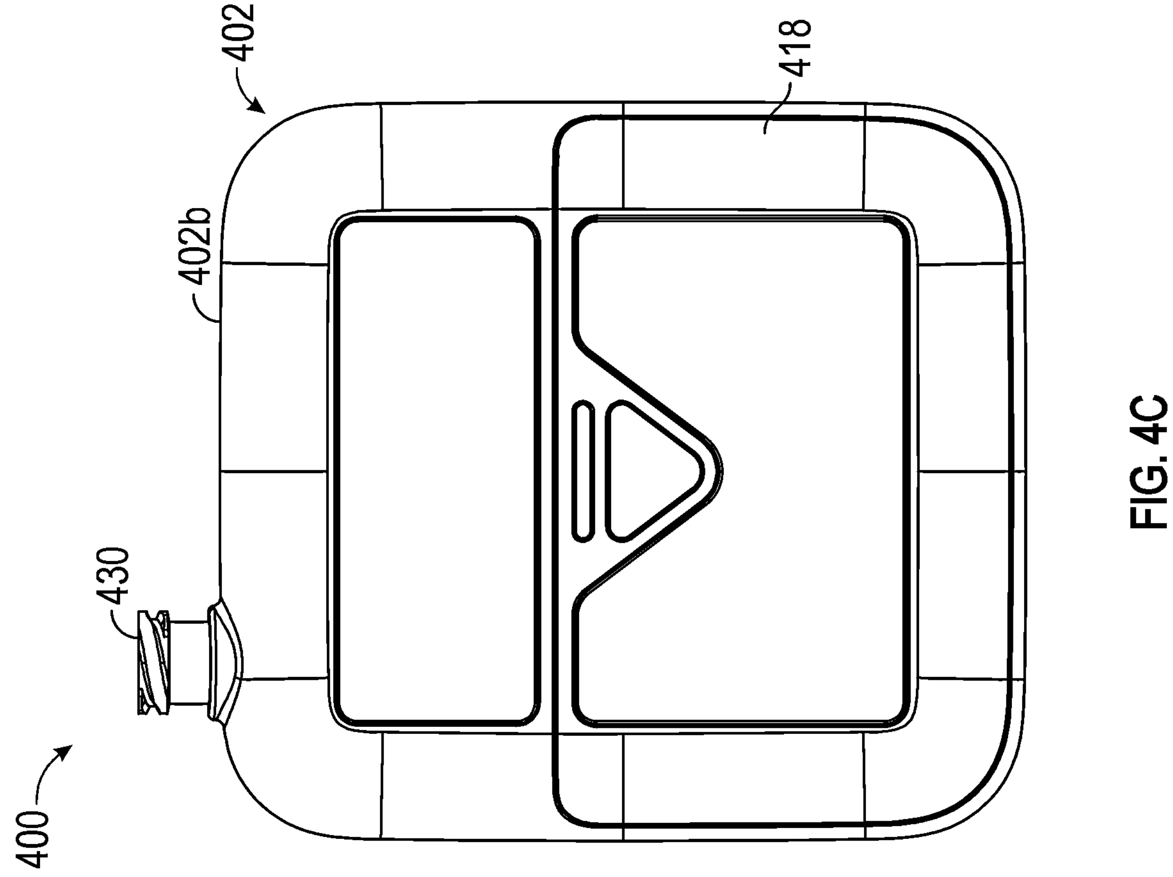

FIGS. 4A, 4B, and 4C illustrate perspective, front, and rear views of a negative pressure wound therapy device 400 (sometimes referred to as a wound therapy device). The wound therapy device 400 can include a housing 402 and a mounting component 410 (such as an attachment). The mounting component 410 can be removably attached to the housing 402, such that the wound therapy device 400 can be used with or without the mounting component 410. For example, FIG. 4C illustrates the wound therapy device 400 without the mounting component 410. The mounting component 410 can be designed to allow the wound therapy device 400 to be mounted on another object such as, but not limited to, a user's person. The mounting component 410 can include a clip 404 designed to retain the mounting component 410 on a user's outerwear, such as on a user's pocket, a pouch, a belt, a flap, or otherwise.

The housing 402 (sometimes referred to as "outer housing") can contain or support components of the wound therapy device 400. The housing 402 can be formed from one or more portions, such as a front portion 402A and a rear portion 402B, which can be removably attached to form the housing 402.

The housing 402 can include a user interface 412 which can be designed to provide a user with information (for example, information regarding an operational status of the wound therapy device 400). The user interface 412 can include one or more indicators, such as icons 414, which can alert the user to one or more operating or failure conditions of the reduced pressure wound therapy system.

The wound therapy device 400 can include one or more user input features, such as button 416, designed to receive an input from the user for controlling the operation of the wound therapy device 400. A single button can be present which can be used to activate and deactivate the reduced pressure wound therapy device or control other operating parameters of the wound therapy device 400.

The wound therapy device 400 can include a connector 430 for connecting a tube or conduit to the wound therapy device 400. The connector 430 can be used to connect the wound therapy device 400 to a wound dressing.

The wound therapy device 400 can be a canisterless device. The wound dressing can retain fluid (such as, exudate) aspirated from the wound. Such a dressing can include a filter, such as a hydrophobic filter, that prevents passage of liquids downstream of the wound dressing (toward the wound therapy device 400).

The wound therapy device 400 can include a cover 418, as illustrated in FIG. 4C and which can be removable. The cover 418 can cover a cavity (not shown) in which one or more power sources, such as batteries, for powering the wound therapy device 400 are positioned.

The wound therapy device 400 can include one or more controllers or other electronic components described herein, such as in connection with FIG. 3. The wound therapy device 400 can be similar to the Pico negative pressure wound therapy device manufactured by Smith & Nephew.

Any of the negative pressure wound therapy devices described herein can include one or more features disclosed in U.S. Patent Publication No. 2019/0231939, which is incorporated by reference in its entirety.

Delivery of Negative Pressure Wound Therapy

Figure 5:
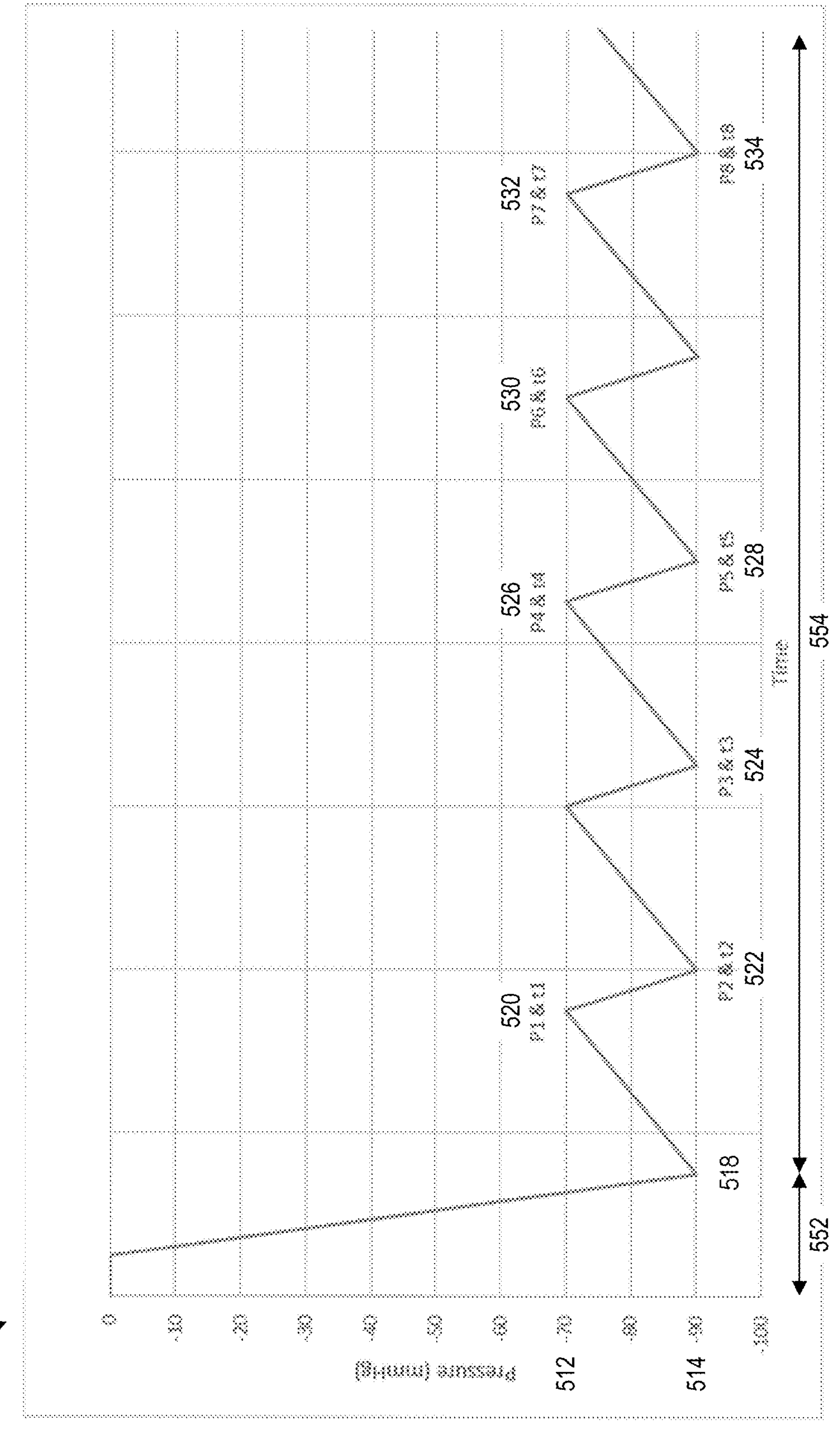
FIG. 5 illustrates a plot of pressure change over time of a negative pressure wound therapy device.

FIG. 5 illustrates a plot 500 of a pressure change over time in a fluid flow path of a negative pressure wound therapy device, such as the wound therapy device 200 or 400. The device can control the source of negative pressure to maintain pressure in the fluid flow path (and at the wound) between a high negative pressure set point 514 and a low negative pressure set point 512. The device can accomplish this via, for instance, one or more controllers (such as, the pump control processor 370).

As illustrated, the high negative pressure set point 514 can be about −90 mmHg (or less or more), and the low negative pressure set point 512 can be about −70 mmHg (or less or more). The high negative pressure set point 514 can be established by activating the source of negative pressure following initialization of negative pressure wound therapy or pause in delivery of therapy. The high negative pressure set point 514 can be reached over time period 552, which can be referred to as initial pump down (IPD) mode. After negative pressure in the fluid flow path has reached (or exceeded) the high negative pressure set point 512 at time 518, the source of negative pressure can be deactivated (for example, in order to one or more of conserve power, reduce noise, or the like). Due to one or more inherent leaks in the fluid flow path, such as through the seal of the wound dressing, through one or more lumens or tubes, or the like, negative pressure can be reduced (or become more positive) over time. In response to the negative pressure reaching (or falling below) the low negative pressure set point 512 at time 520, the source of negative pressure can be activated to reestablish the high negative pressure set point 514. In response to negative pressure in the fluid flow path reaching the high negative pressure set point 514 at time 522, the source of negative pressure can be deactivated. This cycle of negative pressure source activations and deactivations can continue over time period 554, which can be referred to as maintenance mode.

Additional details of delivering negative pressure wound therapy and/or controlling the negative pressure source, which may be implemented by any of the disclosed negative pressure wound therapy devices, are described in one or more of U.S. Pat. No. 8,734,425 or U.S. Pat. No. 8,905,985, each of which is incorporated by reference in its entirety.

Wound Volume Measurement

Any of the systems, apparatuses, or devices disclosed herein, such as the wound therapy device 200 or 400, can be configured to measure and/or monitor volume of a wound (or multiple wounds in case of a system that treats multiple wounds). This can be advantageous for assessing progress of wound healing, alert to any deterioration in the wound, or the like. For example, wound volume can be determined at multiple time points throughout course of therapy (such as, during provision of negative pressure wound therapy). Indication of wound volume can be provided, for instance, visually, audibly, tactilely, or the like. In some cases, wound volumes determined over a duration of time can be plotted to provide an indication of the wound healing trajectory. In certain cases, wound volume can be calculated at each dressing change in order to present the change in real-time or substantially real-time to a health care provider (HCP), such as, doctor, nurse, or the like, performing the dressing change.

As described herein, the fluid flow path can include one or more of the source of negative pressure, canister (when present), one or more lumens or tubes connecting the negative pressure source and/or canister to the wound, and wound dressing. Volume of one or more of such components can be known a priori. Fluid flow path can also include the wound, whose volume may be unknown and changing over time as therapy is being provided to heal the wound. Using any of the approaches described herein, volume of the wound can be determined and/or monitored over time. Because volume of one or more of the source of negative pressure, canister (if present), one or more lumens or tubes connecting the negative pressure source and/or the canister to the wound, and wound dressing can be static and known a priori, such one or more volumes can be subtracted during determination of the wound volume and/or monitoring the change in the wound volume over time.

In some cases, a negative pressure wound therapy system can be closed such that the fluid flow path does not include any orifices, openings, vents, or the like that permit fluid or gas from the external environment or from another external source to enter the fluid flow path (for example, atmospheric air, fluid from an external source of fluid, negative pressure from an external source, or the like). In certain cases, a negative pressure wound therapy system can be partially closed such that the fluid flow path includes at least one orifice, opening, vent, or the like that permits fluid or gas from the external environment or from another external source to enter the fluid flow path. A partially closed system can additionally or alternatively include a leak through the dressing. Such orifice, opening, vent, dressing leak, or the like can be referred to as a controlled leak source. For example, a port (such as, Renasys Soft Port manufactured by Smith & Nephew) connecting the source of negative pressure to the wound dressing can include such orifice, opening, vent, or the like. Additional details of such port, which may be implemented by any of the disclosed negative pressure wound therapy devices, are described in U.S. Pat. No. 8,801,685, which is incorporated by reference in its entirety. Rate of fluid flow through any of the controlled leak sources can be referred to as controlled leak rate. It may be advantageous to provide one or more controlled leak sources in the fluid flow path to facilitate uninterrupted or substantially uninterrupted aspiration of fluid from the wound, particularly when slugs of fluid, dense matter, or the like is being aspirated through the fluid flow path.

Volume of a closed or partially closed negative pressure wound therapy system can be determined according to the following equation. This equation may be derived from the ideal gas law.

$$\text{Volume} = (\text{flow rate} \times \text{gas constant} \times \text{temperature} \times (t_2 - t_1))/(P_2 - P_1) \quad (1)$$

In Equation 1, volume can be associated with volume of the system, which can include volume of one or more of the source of negative pressure, canister (when present), one or more lumens or tubes connecting the negative pressure source and/or canister to the wound, wound dressing, and wound. As described herein, volumes of such one or more of source of negative pressure, canister (when present), one or more lumens or tubes connecting the negative pressure source and/or canister to the wound, and wound dressing can be known a priori and subtracted from the volume calculated according to Equation 1 to determine the wound volume.

In a closed system, flow rate can be associated with properties of the negative pressure source, and may be known a priori. Equation 1 may assume that any inherent leak in the system (as described herein) is much smaller than the flow rate. For example, Equation 1 may be applicable for use in a well-sealed system.

Values $t_2$ and $t_1$ can correspond, respectively, to a final time and initial time corresponding to a time period over which volume is being measured. Pressures $P_2$ and $P_1$ can correspond, respectively, to final pressure and initial pressures over such time period (for instance, as measured by one or more pressure sensors). In some cases, pressure $P_2$ can correspond to a higher negative pressure than pressure $P_1$. For example, pressure $P_2$ can correspond to the high negative pressure set point 514 (such as, pressure at time 522 illustrated in FIG. 5), and pressure $P_1$ can correspond to the low negative pressure set point 512 (such as, negative pressure at time 520 as illustrated in FIG. 5). In such cases, wound volume can be determined when the source of negative pressure is active (for example, over a single maintenance pump down cycle).

Gas constant can correspond to $8.3144598\times10^6$ $cm^3\times Pa\times K^{-1}\times mol^{-1}$. Temperature can correspond to temperature of the surrounding environment (for example, room temperature). In some cases, one or more of the gas constant or temperature may not be utilized in the calculation of the volume according to Equation 1 and/or any of the other equations disclosed herein.

Wound volume can be monitored over time following the initial calculation. As described herein, monitoring the wound volume can permit determining the rate of wound healing.

In some cases, one or more of the following constants can be used in Equation 1 and/or any of the other equations disclosed herein:

Density of air at sea level (at 1013 hPa): 0.00120408370680897 g/ml

Molar mass of air: 28.97 g/mol

Temperature measured in Kelvin, where 20 C=291.15 K

The system can have a leak rate (sometimes referred to as leak rate of the system) that can correspond to the controlled leak rate in a partially closed system and/or any inherent leaks in a closed or partially closed system. The leak rate of the system can be determined and factored into the flow rate of Equation 1. This can provide for a more accurate determination of the wound volume. In some cases, volume of the wound can be determined using the leak rate of the system in place of the flow rate in Equation 1. In such cases, it may be assumed that the leak rate through the seal of the wound dressing is constant or substantially constant.

Leak rate of the system can be determined according to the following equation:

$$\text{Leak} = (\text{volume} \times (P_4 - P_3))/(\text{gas constant} \times \text{temperature} \times (t_4 - t_3)) \quad (2)$$

Equation 2 can be derived from Equation 1. In Equation 2, volume can correspond to the volume determined using Equation 1.

In Equation 2, values $t_4$ and $t_3$ can correspond, respectively, to final time and initial time corresponding to a time period over which the leak rate of the system is being measured. Pressures $P_4$ and $P_3$ can correspond, respectively, to final pressure and initial pressures over such time period (for instance, as measured by one or more pressure sensors). In some cases, pressure $P_4$ can correspond to lower negative pressure than pressure $P_3$. For example, $P_4$ can correspond to the low negative pressure set point 512 (such as, pressure at time 526 illustrated in FIG. 5), and pressure $P_3$ can correspond to the high negative pressure set point 514 (such as, negative pressure at time 524 as illustrated in FIG. 5). Gas constant and temperature can be same as or similar as described herein in connection with Equation 1.

In a partially closed system, leak rate of the system may include controlled leak rate (as described herein). Instead of using Equation 2 to determine the leak rate of the system, contributions of the controlled leak rate may be known a priori or be determined, for instance, when the source of negative pressure is deactivated. The leak rate of the system can be determined, for example, using a flow meter. As another example, the leak rate of the system can be determined based on activity of the source of negative pressure. Such activity can be measured using duty cycle of the source of negative pressure, speed of a motor of the source of negative pressure, or the like. Subsequent to the determination of the leak rate of the system, Equation 2 can be used to compare the calculated leak rate of the system against that known a priori or determined without using the volume derived using Equation 1, for instance, in order to verify the accuracy of wound volume calculations.

In a partially closed system, controlled leak rate can be used to determine the volume according to the following equation. This equation is similar to Equation 1 with the exception that controlled leak rate can be used in place of flow rate. Equation 3 may be applicable to systems in which the controlled leak rate is much larger than the rate of any inherent leak.

$$\text{Volume} = (\text{controlled leak} \times \text{gas constant} \times \text{temperature} \times (t_6 - t_5))/(P_6 - P_5) \quad (3)$$

Values $t_6$ and $t_5$ can correspond, respectively, to a final time and initial time corresponding to a time period over which volume is being measured. Pressures $P_6$ and $P_5$ can correspond, respectively, to final pressure and initial pressures over such time period (for instance, as measured by one or more pressure sensors). In some cases, pressure $P_6$ can correspond to a lower negative pressure than pressure $P_5$. For example, pressure $P_6$ can correspond to the low negative pressure set point 512 (such as, pressure at time 530 illustrated in FIG. 5), and pressure $P_5$ can correspond to the high negative pressure set point 514 (such as, negative pressure at time 528 as illustrated in FIG. 5). In such cases, wound volume can be determined when the source of negative pressure is inactive (for example, when negative pressure is being reduced as a result of any of the controlled leak sources). Gas constant and temperature can be same as or similar as described herein in connection with Equation 1.

The flow rate of the device, which may correspond to the controlled leak rate, can be verified using the following equation.

$$\text{Flow rate} = (\text{volume} \times (P_8 - P_7))/(\text{gas constant} \times \text{temperature} \times (t_8 - t_7)) \quad (4)$$

Equation 4 can be derived from Equation 3. In Equation 4, volume can correspond to the volume determined using Equation 3. Equation 4 can be used, for instance, to verify the accuracy of wound volume calculations.

Values $t_8$ and $t_7$ can correspond, respectively, to a final time and initial time corresponding to a time period over which volume is being measured. Pressures $P_8$ and $P_7$ can correspond, respectively, to final pressure and initial pressures over such time period (for instance, as measured by one or more pressure sensors). In some cases, pressure $P_8$ can correspond to a higher negative pressure than pressure $P_7$. For example, pressure $P_8$ can correspond to the high negative pressure set point 514 (such as, pressure at time 534 illustrated in FIG. 5), and pressure $P_7$ can correspond to the low negative pressure set point 512 (such as, negative pressure at time 532 as illustrated in FIG. 5). In such cases, wound volume can be determined when the source of negative pressure is active (for example, over a single maintenance pump down cycle). Gas constant and temperature can be same as or similar as described herein in connection with Equation 1.

In a system in which a flow rate is much larger than the leak rate (such as, the inherent leak rate), change in the volume of the wound can be determined according to the following equation. In some cases, the below equation can be utilized in system with a substantially constant flow rate. The change in the volume of the wound can be determined as a percentage.

$$\text{Change in Wound Volume} = ((V_2 - V_5)/V_5) \times 100\% = ((t_2 - t_5)/t_5) \times 100\% \quad (5)$$

Values $t_5$ and $t_2$ can correspond, respectively, to a final time and initial time corresponding to a time period over which the change in the volume of the wound is being measured. For example, times $t_5$ and $t_2$ can correspond to the times at which the high negative pressure set point 514 has been satisfied. As illustrated in FIG. 5, time $t_5$ can correspond to time 528, and time $t_2$ can correspond to time 522. In such cases, Equation 5 can be used to determine the change in the volume of the wound based on a duration of time for reestablishing the high negative pressure set point in the fluid flow path (such as, time duration over one or more maintenance pump downs cycles).

Final and initial times in Equation 5 can selected as a pair of times associated with any pair of similar events, such as any pair of times at which the high pressure set point 514 has been satisfied or any pair of times at which the low negative pressure set point 512 has been reached. For example, the final and initial times can be selected, respectively, as times $t_6$ (corresponding to time 530 in FIG. 5) and $t_1$ (corresponding to time 520 in FIG. 5). In such cases, Equation 5 can be used to determine the change in the volume of the wound based on a duration of time associated with loss of negative pressure due to one or more leaks.

Disclosed approaches for measuring and/or monitoring volume of the wound can be used to generally measure and/or monitor changes in the system volume for any medical or non-medical device. Disclosed approaches can be used in systems that, in addition to or instead of negative pressure wound therapy, supply positive pressure, for example, via instillation of one or more fluids. Discloses approaches can be used as a standalone wound measuring device, which may not be incorporated into an existing medical or non-medical device.

Figure 6:
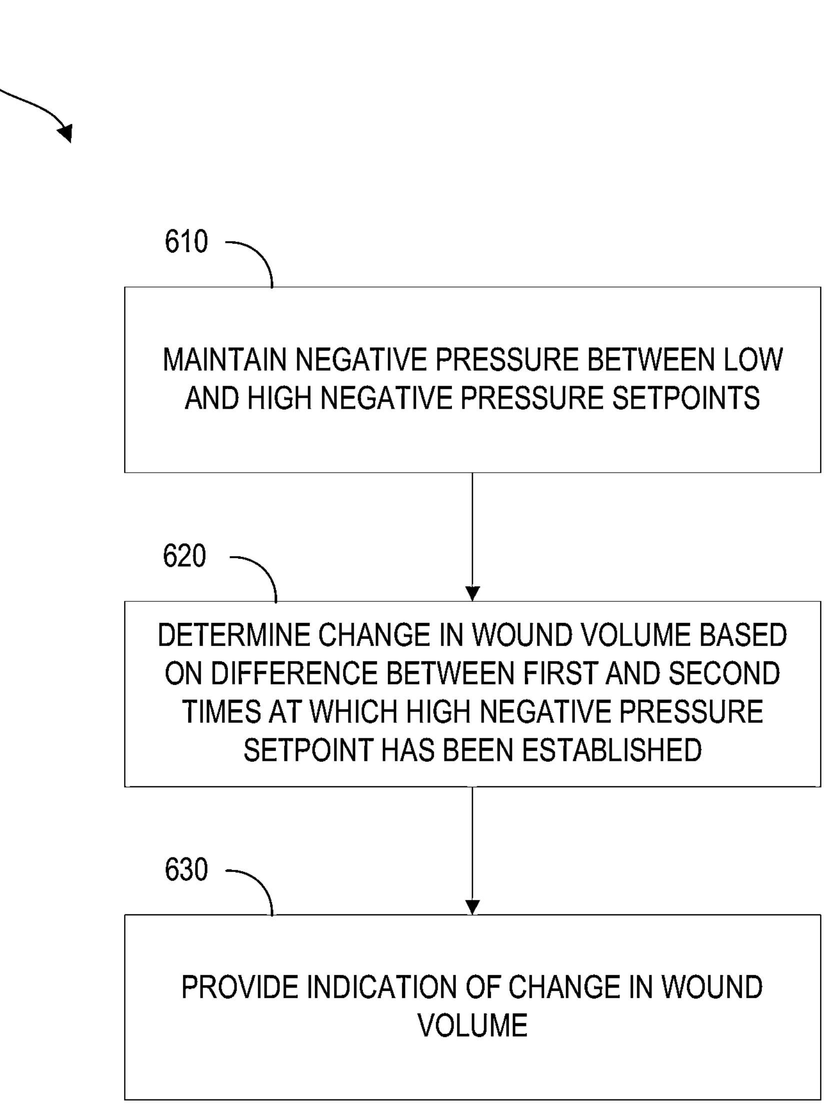
FIGS. 6 and 7 illustrate processes for determining wound volume.

FIG. 6 illustrates a process 600 for determining wound volume. The process 600 can be implemented by any of the systems, apparatuses, or devices disclosed herein, such as the wound therapy device 200 or 400. The process 600 can be executed by a controller. At block 610, the process 600 can maintain negative pressure in a fluid flow path between a low negative pressure setpoint and a high negative pressure setpoint by periodically activating a negative pressure source. The high negative pressure setpoint can be associated with a higher level of negative pressure than the low negative pressure setpoint. At block 620, the process 600 can determine a change in a volume of the wound based on a difference between a first time and a second time at which the high negative pressure setpoint has been established in the fluid flow path. The second time can be subsequent to the first time. At block 630, the process can provide indication of the change in the volume of the wound.

Figure 7:
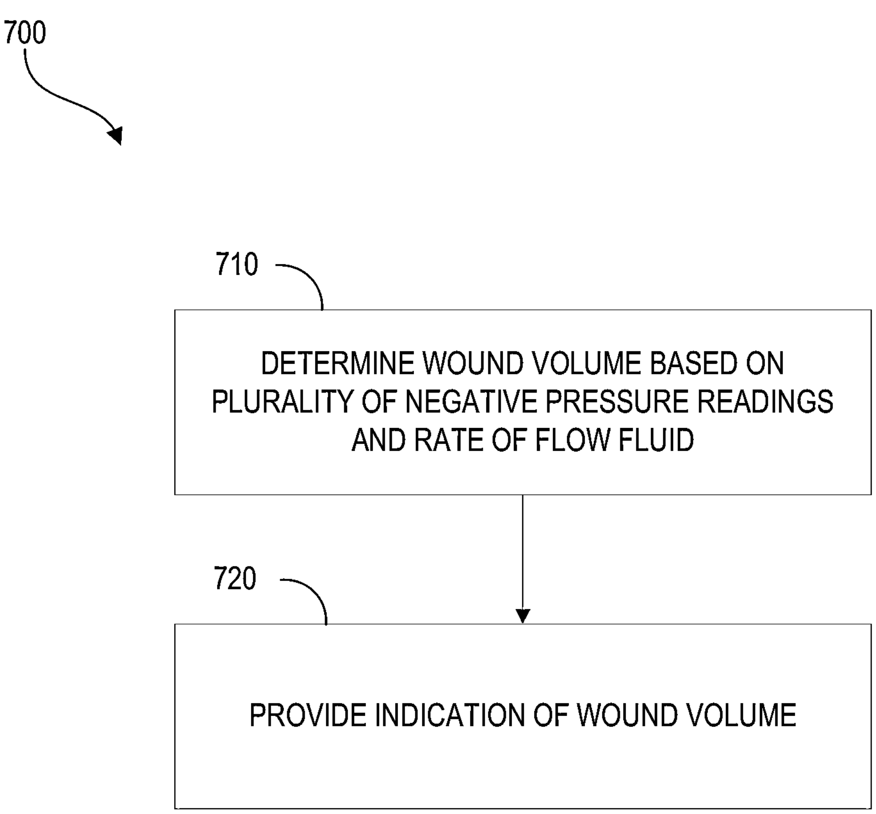

FIG. 7 illustrates a process 700 for determining wound volume. The process 700 can be implemented by any of the systems, apparatuses, or devices disclosed herein, such as the wound therapy device 200 or 400. The process 700 can be executed by a controller. At block 710, the process 700 can determine a volume of the wound based on a first plurality of negative pressure readings in a fluid flow path measured at a plurality of times and a rate of flow of fluid in the fluid flow path. At block 720, the process 700 can provide indication of the volume of the wound.

Any of the disclosed approaches for measuring and/or monitoring volume of the wound can include one or more wound volume measurement features disclosed in U.S. Pat. No. 8,814,841, which is incorporated by reference in its entirety.

Leak Detection

Equation 2 can be used to determine the leak rate and/or indicate a leak condition. Such determination can be made subsequent to the determination of volume, for instance, with Equation 1. Leak condition can be indicated based on determining that the leak rate obtained with Equation 2 satisfies one or more leak thresholds.

Additionally or alternatively, Equation 4 can be used to determine the leak rate and/or indicate a leak condition. Such determination can be made subsequent to the determination of volume, for instance, with Equation 3. Leak condition can be indicated based on determining that the leak rate obtained with Equation 4 exceeds the controlled leak rate by one or more thresholds.

Other Variations

Although some embodiments describe negative pressure wound therapy, the systems, devices, and/or methods disclosed herein can be applied to other types of therapies usable standalone or in addition to TNP therapy. Systems, devices, and/or methods disclosed herein can be extended to any medical device, and in particular any wound treatment device. For example, systems, devices, and/or methods disclosed herein can be used with devices that provide one or more of ultrasound therapy, oxygen therapy, neurostimulation, microwave therapy, active agents, antibiotics, antimicrobials, or the like. Such devices can in addition provide TNP therapy. The systems and methods disclosed herein are not limited to medical devices and can be utilized by any electronic device.

Any of transmission of data described herein can be performed securely. For example, one or more of encryption, https protocol, secure VPN connection, error checking, confirmation of delivery, or the like can be utilized.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Conditional language used herein, such as, among others, "can," "could", "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A method of operating a negative pressure wound therapy apparatus comprising:

periodically activating a negative pressure source to maintain negative pressure in a fluid flow path connecting the negative pressure source to a wound covered by a wound dressing between a low negative pressure setpoint and a high negative pressure setpoint, the high negative pressure setpoint being associated with higher level of negative pressure than the low negative pressure setpoint;

determining a change in a volume of the wound based on a time duration between a first time at which the high negative pressure setpoint has been established and a second time at which the high negative pressure setpoint has been reestablished in the fluid flow path, the second time being subsequent to the first time; and providing indication of the change in the volume of the wound, wherein the method is performed by a controller of the negative pressure wound therapy apparatus.

2. The method of claim 1, further comprising:

monitoring the change in the volume of the wound over a duration of time; and providing indication of progress of healing of the wound based on the change in the volume of the wound monitored over the duration of time.

3. The method of claim 1, further comprising determining the change in the volume of the wound based on a difference between the first time and the second time divided by the second time.

4. The method of claim 1, further comprising:

determining that negative pressure in the fluid flow path satisfies the high negative pressure setpoint; and deactivating the negative pressure source responsive to determining that negative pressure in the fluid flow path satisfies the high negative pressure setpoint.

5. The method of claim 1, further comprising:

determining that negative pressure in the fluid flow path satisfies the low negative pressure setpoint; and activating the negative pressure source responsive to determining that negative pressure in the fluid flow path satisfies the low negative pressure setpoint.

6. The method of claim 1, wherein determining the change in the volume of the wound is performed without determining a rate of leak in the fluid flow path.

7. The method of claim 1, wherein the fluid flow path is configured to not include any openings configured to admit fluid into the fluid flow path at a controlled leak rate.

8. A method of operating a negative pressure wound therapy apparatus comprising:

determining a volume of a wound based on a first plurality of negative pressure measurements in a fluid flow path connecting a negative pressure source to the wound covered by a wound dressing and a rate of flow of fluid in the fluid flow path, the first plurality of negative pressure measurements being made at a first plurality of times, the first plurality of negative pressure measurements comprising first and second negative pressure measurements made, respectively, at first and second times, the second time being subsequent to the first time, and the second negative pressure measurement corresponding to pressure that is more negative than the first negative pressure measurement; and providing indication of the volume of the wound, wherein the method is performed by a controller of the negative pressure wound therapy apparatus.

9. The method of claim 8, further comprising, by the controller:

monitoring a change in the volume of the wound over a duration of time; and providing indication of progress of healing of the wound based on the change in the volume of the wound monitored over the duration of time.

10. The method of claim 8, wherein determining the volume of the wound is performed using a product of the rate of flow of fluid in the fluid flow path and a difference between the second and first times divided by a difference between the second and first negative pressure measurements.

11. The method of claim 10, wherein the product is scaled by at least one of an ambient temperature or gas constant.

12. The method of claim 8, further comprising:

determining a leak rate in the fluid flow path; and determining the volume of the wound based on the first plurality of negative pressure measurements in the fluid flow path made at the first plurality of times and an adjusted rate of flow of fluid in the fluid flow path, the adjusted rate of flow of fluid in the fluid flow path being determined based on subtracting the leak rate from the rate of flow of fluid in the fluid flow path.

13. The method of claim 12, further comprising:

determining the leak rate in the fluid flow path based on the volume of the wound and a second plurality of negative pressure measurements in the fluid flow path made at a second plurality of times, the second plurality of negative pressure measurements including third and fourth negative pressure measurements made, respectively, at third and fourth times, the fourth time being subsequent to the third time, and the fourth negative pressure measurement corresponding to pressure that is more positive than the third negative pressure measurement.

14. The method of claim 13, wherein determining the leak rate is performed using a product of the volume of the wound and a difference between the fourth and third negative pressure measurements divided by a difference between the fourth and third times.

15. The method of claim 14, wherein the difference between the fourth and third times is scaled by at least one of an ambient temperature or gas constant.

16. The method of claim 8, wherein determining the volume of the wound is performed without determining a rate of leak in the fluid flow path.

17. The method of claim 8, further comprising:

determining a first leak rate in the fluid flow path based on the volume of the wound;

determining a second leak rate in the fluid flow path using a flow meter or based on a level of activity of the negative pressure source; and verifying that the volume of the wound has been accurately determined based on a determination that the first leak rate matches the second leak rate.

18. The method of claim 8, further comprising, by the controller:

determining a leak rate in the fluid flow path based on the volume of the wound; and verifying that the volume of wound has been accurately determined based on a determination that first leak rate matches a known leak rate in the fluid flow path.

19. The method of claim 8, further comprising, by the controller:

periodically activating the negative pressure source to maintain negative pressure in the fluid flow path between a low negative pressure setpoint and a high negative pressure setpoint, the high negative pressure setpoint being associated with higher level of negative pressure than the low negative pressure setpoint.

20. The method of claim 19, wherein periodically activating the negative pressure source to maintain negative pressure in the fluid flow path between the low negative pressure setpoint and the high negative pressure setpoint comprises:

at a first time, determining that negative pressure in the fluid flow path satisfies the low negative pressure setpoint and activating the negative pressure source responsive to determining that negative pressure in the fluid flow path satisfies the low negative pressure setpoint; and at a second time, determining that negative pressure in the fluid flow path satisfies the high negative pressure setpoint and deactivating the negative pressure source in response to determining that negative pressure in the fluid flow path measured satisfies the high negative pressure setpoint.

* * * * *